United States Patent
Allen et al.

(12)

(10) Patent No.: US 8,501,137 B2
(45) Date of Patent: Aug. 6, 2013

(54) PROCESS FOR PRODUCTION OF AN ALUMINUM HYDRIDE COMPOUND

(75) Inventors: Nathan Tait Allen, Philadelphia, PA (US); Robert Butterick, III, Swedesboro, NJ (US); Arthur Achhing Chin, Cherry Hill, NJ (US); Dean Michael Millar, Midland, MI (US); David Craig Molzahn, Midland, MI (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 268 days.

(21) Appl. No.: 13/053,356

(22) Filed: Mar. 22, 2011

(65) Prior Publication Data

US 2011/0236287 A1    Sep. 29, 2011

Related U.S. Application Data

(60) Provisional application No. 61/317,949, filed on Mar. 26, 2010.

(51) Int. Cl.
*C01B 35/00* (2006.01)
*C07F 5/06* (2006.01)

(52) U.S. Cl.
USPC ............. 423/288; 556/179; 556/181

(58) Field of Classification Search
USPC .................. 556/179, 181; 423/288
See application file for complete search history.

(56) References Cited

U.S. PATENT DOCUMENTS

| | | | |
|---|---|---|---|
| 3,184,492 A | 5/1965 | Marc |
| 3,257,455 A | 6/1966 | Ashby |
| 3,290,393 A | 12/1966 | Marchand |
| 3,394,158 A | 7/1968 | Chini |
| 3,507,895 A | 4/1970 | Bohuslav |
| 3,728,272 A | 4/1973 | Casensky |
| 7,247,286 B2 | 7/2007 | Ashby |

FOREIGN PATENT DOCUMENTS

| | | |
|---|---|---|
| EP | 327473 | 9/1989 |
| EP | 2 368 893 A1 * | 9/2011 |
| JP | 4292401 | 10/1992 |

OTHER PUBLICATIONS

Gavrilenko et al., Izestiya Akademii Nauk SSSR, Seriya Khimicheskaya, vol. 4, pp. 865-869 (1984).*

* cited by examiner

*Primary Examiner* — Porfirio Nazario Gonzalez
(74) *Attorney, Agent, or Firm* — Kenneth Crimaldi

(57) ABSTRACT

A compound of formula $M(AlH_3OR^1)_y$, wherein $R^1$ is phenyl substituted by at least one of: (i) an alkoxy group having from one to six carbon atoms; and (ii) an alkyl group having from three to twelve carbon atoms; wherein M is an alkali metal, Be or Mg; and y is one or two.

8 Claims, No Drawings

PROCESS FOR PRODUCTION OF AN ALUMINUM HYDRIDE COMPOUND

This application claims the benefit of priority under 35 U.S.C. §119(e) of U.S. Provisional Patent Application No. 61/317,949 filed on Mar. 26, 2010.

This invention was made with Government support under Contract No. DE-FC36-05GO15053 awarded by the Department of Energy. The Government has certain rights in this invention.

BACKGROUND

This invention relates generally to a novel aluminum hydride compound and a process for its production. The aluminum hydride compound is useful in production of borohydrides.

Sodium trihydridoaluminum aryloxide compounds are described in U.S. Pat. No. 3,507,895. However, this reference does not disclose the compounds claimed herein and it also discloses an inefficient process for production of these compounds requiring use of metallic sodium.

The problem addressed by this invention is to find an efficient and economical process for production of an aluminum hydride compound without use of metallic sodium.

STATEMENT OF INVENTION

The present invention is directed to a compound of formula $M(AlH_3OR^1)_y$, wherein $R^1$ is phenyl substituted by at least one of: (i) an alkoxy group having from one to six carbon atoms; and (ii) an alkyl group having from three to twelve carbon atoms; wherein M is an alkali metal, Be or Mg; and y is one or two.

The present invention is further directed to a process for production of a compound of formula $M(AlH_3OR^2)_y$, wherein $R^2$ is phenyl or phenyl substituted by at least one alkyl or alkoxy group, M is an alkali metal, Be or Mg, and y is one or two. The process comprises combining a compound of formula $(R^2O)_yM$ with aluminum, hydrogen and a metallic catalyst comprising at least one metal selected from the group consisting of titanium, zirconium, hafnium, niobium, vanadium, tantalum and iron; wherein the catalyst is present at a level of at least 200 ppm metal based on weight of aluminum.

DETAILED DESCRIPTION

All percentages are weight percentages ("wt %") and temperatures are in ° C., unless specified otherwise. An "alkyl" group is a saturated hydrocarbyl group having from one to twelve carbon atoms in a linear, branched or cyclic arrangement. Preferably, alkyl groups are acyclic; preferably $C_1$-$C_{12}$ acyclic; preferably $C_1$-$C_6$ acyclic. A "naphthanol" group is a group derived by removal of a hydrogen atom from the hydroxy group of 1-naphthol or 2-naphthol.

Preferably, M is an alkali metal and y is one; preferably the alkali metal is lithium, sodium or potassium; preferably sodium or potassium; preferably sodium.

Preferably, $R^1$ is phenyl substituted by at least one of: (i) an alkoxy group having from one to four carbon atoms; and (ii) an alkyl group having from three to six carbon atoms; preferably by at least one of: (i) an alkoxy group having from one to three carbon atoms; and (ii) an alkyl group having from three to four carbon atoms. Preferably, $R^1$ is phenyl substituted by an alkoxy group having from one to four carbon atoms, preferably methoxy or ethoxy, preferably methoxy. Preferably, $R^1$ is 4-methoxyphenyl; 2-methoxyphenyl; 3-methoxyphenyl; 4-ethoxyphenyl; 2-ethoxyphenyl; 3-ethoxyphenyl; 4-isopropylphenyl; 2-isopropylphenyl; 3-isopropylphenyl; 2,6-di-t-butyl-4-methylphenyl; 2,6-di-t-butyl-4-methoxyphenyl; 2,6-di-t-butyl-4-ethylphenyl; 2,4-di-t-butylphenyl; 2,5-di-t-butyl-4-methoxyphenyl; or 2,6-di-isopropylphenyl. Preferably, R' is 4-methoxyphenyl; 2,6-di-t-butyl-4-methylphenyl; or 2,6-di-t-butyl-4-methoxyphenyl; preferably 4-methoxyphenyl. Preferably, $R^2$ is phenyl or phenyl substituted by at least one of: (i) an alkoxy group having from one to four carbon atoms; and (ii) an alkyl group having from one to four carbon atoms. Preferably, $R^2$ is not phenyl or phenyl substituted by methyl. Preferably, $R^2$ is phenyl substituted by an alkoxy group having from one to four carbon atoms, preferably methoxy or ethoxy, preferably methoxy. Preferably, $R^2$ is phenyl; 4-methylphenyl; 2-methylphenyl; 3-methylphenyl; 4-methoxyphenyl; 2-methoxyphenyl; 3-methoxyphenyl; 4-ethoxyphenyl; 2-ethoxyphenyl; 3-ethoxyphenyl; 4-isopropylphenyl; 2-isopropylphenyl; 3-isopropylphenyl; 2,6-di-t-butyl-4-methylphenyl; 2,6-di-t-butyl-4-methoxyphenyl; 2,6-di-t-butyl-4-ethylphenyl; 2,4-di-t-butylphenyl; 2,5-di-t-butyl-4-methoxyphenyl; or 2,6-di-isopropylphenyl. Preferably, $R^2$ is phenyl; 4-methylphenyl; 4-methoxyphenyl; 2,6-di-t-butyl-4-methylphenyl; or 2,6-di-t-butyl-4-methoxyphenyl.

The reaction of the compound of formula $(R^2O)_yM$ with aluminum, hydrogen and a metallic catalyst is illustrated in the following equation, in which $R^2$ is 4-methoxyphenyl, M is sodium and the metallic catalyst is titanium:

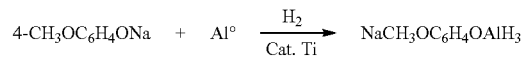

Preferably, the metallic catalyst comprises titanium, zirconium, hafnium or combinations thereof; preferably titanium. Preferably, the metallic catalyst is incorporated into the aluminum at a level of at least 240 ppm based on weight of aluminum, preferably at least 280 ppm, preferably at least 300 ppm, preferably at least 320 ppm, preferably at least 340 ppm. Preferably, the metallic catalyst is incorporated into the aluminum at a level no greater than 10,000 ppm based on weight of aluminum, preferably no greater than 5,000 ppm. Preferably, the metallic catalyst may be added as a compound of the metal at the same levels stated above. When the metallic catalyst is titanium, it may be added as an alloy in the aluminum, as a compound of titanium such as titanium(IV)isopropoxide or titanium(IV) chloride or as free titanium metal. Preferably, the mole ratio of aluminum to $(R^2O)_yM$ is at least 0.9:1, preferably at least 0.95:1, preferably at least 1:1; preferably the ratio is no greater than 2:1, preferably no greater than 1.5:1, preferably no greater than 1.2:1. When y is two, these mole ratios would be double the aforementioned numbers. However, when the reaction is carried out with flow of other reactants through aluminum in a fixed bed, one skilled in the art will understand that the amount of aluminum present in relation to the reaction solution in the bed will be much larger. Preferably, the aluminum has an average particle size from 50 to 1000 microns, preferably from 75 to 700 microns. Preferably, the reaction of a compound of formula $(R^2O)_yM$, wherein M is an alkali metal, Be or Mg, with aluminum, hydrogen and a metallic catalyst proceeds under an absolute pressure of at least 300 psi (2 MPa), alternatively at least 500 psi (3.4 MPa), alternatively at least 700 psi (4.8 MPa). Preferably, the reaction proceeds at a pressure no greater than 1500 psi (10.3 MPa), alternatively no greater than 1200 psi (8.3 MPa). Preferably, the reaction proceeds at a temperature of at least 90° C., preferably at least 110° C., preferably at least 130° C., preferably at least 150° C. Preferably, the reaction proceeds at a temperature no greater than 200° C., preferably no greater than 180° C., preferably no greater than 170° C.

The reaction of $(R^2O)_yM$ with aluminum and hydrogen in the presence of a metallic catalyst may proceed in a solvent or as a slurry reaction. Solvents suitable for the reaction of $(R^2O)_yM$ with aluminum and hydrogen in the presence of a metallic catalyst include ethers, e.g., diglyme, tetraglyme, diethyl ether, dibutyl ether, dibutyl diglyme, tetrahydrofuran, dimethoxyethane, and 2-methyltetrahydrofuran; and aromatic solvents, e.g., benzene, toluene and xylenes. The concentration is not critical, although it is preferred that the $R^2OM$ is dissolved completely in the solvent. The same solvents would be suitable for a slurry reaction.

Preferably, the compound $M(AlH_3OR^2)_y$ or $M(AlH_3OR^1)_y$ is combined with a borate, boroxine or borazine compound to produce an alkali metal borohydride, preferably a borate or boroxine compound. Preferably, the borate or boroxine compound is a trialkyl or triaryl borate or boroxine. Preferably, the borate or boroxine which reacts with $M(AlH_3OR^2)_y$ or $M(AlH_3OR^1)_y$, respectively, contains three $R^2O-$ or $R^1O-$ groups. This reaction is illustrated in the following equation, in which $R^2$ is 4-methoxyphenyl, M is sodium and the reactant is a boroxine:

$$4Na[CH_3OC_6H_4OAlH_3]+(CH_3OC_6H_4OBO)_3 \rightarrow 3NaBH_4+3CH_3OC_6H_4AlO+Na[AlOC_6H_4OCH_3)_4]$$

This reaction also proceeds with the corresponding triaryl borate, $(4-CH_3OC_6H_4O)_3B$. Preferred solvents for this reaction are those in which sodium borohydride has limited solubility, e.g., ethers, including 2-methyl-tetrahydrofuran, tetrahydrofuran, dimethoxyethane, diglyme, triglyme, tetraglyme, diethyl ether, dibutyl ether and dibutyl diglyme; aromatic solvents; and alkanes. Especially preferred solvents include 2-methyl-tetrahydrofuran, tetrahydrofuran and dimethoxyethane. Preferably, this reaction proceeds at a temperature in the range from 0° C. to 50° C., preferably from 10° C. to 35° C. Preferably, sodium borohydride precipitates from the reaction solvent and is separated, while the aryl oxide salts remain in solution.

The compound $M(AlH_3OR^2)_y$ or $M(AlH_3OR^1)_y$ may contain varying amounts of other related species having the formula $M(AlH_{4-x}(OR)_x)_y$, where x is an integer from zero to four and R is $R^1$ and/or $R^2$. Varying amounts of $M(AlH_4)_y$ may be present. Species in which x is equal to zero, two or three are also reactive with boroxines or borates. However, it is preferred that the ratio of aluminum to aryl oxide ($OR^1$ or $OR^2$) is from 0.5 to 2, preferably from 0.7 to 1.5, preferably 0.8 to 1.2.

Preferably, the aryl oxide species formed along with the alkali metal borohydride are separated from the borohydride and treated with water or an aqueous acid, preferably a mineral acid, to regenerate the phenol or substituted phenol for recycling. The phenol or substituted phenol is combined with boric acid (or meta-boric acid or boron oxide) or a trialkyl borate to form a triaryl borate, $(ArO)_3B$, or triaryl boroxine, $(ArOBO)_3$, depending on the stoichiometry and temperature of the reaction. The reaction to form the boroxine is illustrated below for the case where the substituted phenol is 4-methoxyphenol

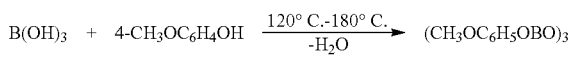

A solvent may be used to separate the borohydride product. Suitable solvents are those in which the borohydride compound is soluble and which are relatively unreactive with borohydride. A solvent in which the borohydride compound is soluble is one in which the borohydride compound is soluble at 25° C. at least at the level of 2%, preferably, at least 5%. Preferred solvents include liquid ammonia, alkyl amines (primary and secondary), heterocyclic amines, alkanolamines, alkylene diamines, glycol ethers, amide solvents (e.g., heterocyclic amides and aliphatic amides), dimethyl sulfoxide and combinations thereof. Preferably, the solvent is substantially free of water, e.g., it has a water content less than 0.5%, more preferably less than 0.2%; with the exception that concentrated (30-45%) aqueous alkali metal hydroxide solution may be used due to the known stability of borohydrides in this medium, e.g., sodium or potassium hydroxide at approximately 40%. Especially preferred solvents include ammonia, $C_1-C_4$ mono-alkyl amines, pyridine, 1-methyl-2-pyrrolidone, 2-aminoethanol, ethylene diamine, ethylene glycol dimethyl ether, diethylene glycol dimethyl ether, triethylene glycol dimethyl ether, tetraethylene glycol dimethyl ether, dimethylformamide, dimethylacetamide, dimethylsulfoxide and combinations thereof.

The reaction may also be run without a solvent, e.g., as a slurry process or by grinding the solid reactants. Grinding of the reactants will accelerate the reaction, and may be achieved using any method which applies energy to solid particles to induce a mechanochemical reaction, especially any method which reduces solids to the micron size range, preferably the sub-micron size range, and continually exposes fresh surfaces for reaction, e.g., impact, jet or attrition milling. Preferred methods include ball milling, vibratory (including ultrasonic) milling, air classifying milling, universal/pin milling, jet (including spiral and fluidized jet) milling, rotor milling, pearl milling. Especially preferred methods are planetary ball milling, centrifugal ball milling, and similar types of high kinetic energy rotary ball milling. Preferably, milling is performed in either a hydrogen atmosphere, or an inert atmosphere, e.g., nitrogen. In an embodiment in which a solvent is used, grinding of the reactants may be achieved using any method suitable for grinding a slurry. A solvent facilitates heat transfer, thereby minimizing hot spots and allowing better temperature control. Recycle of the solvent is possible to improve process economics. Examples of solvents suitable for use during the process include amines, especially tertiary amines; alkanes and cycloalkanes, especially $C_8-C_{12}$ alkanes and cycloalkanes; ionic liquids; liquid crown ethers; and for lower-temperature reaction conditions, toluene, glymes and ethers. Suitable reaction solvents are those in which the borohydride compound is soluble and which are relatively unreactive with borohydride.

Another method to accelerate the reaction is to use radiation techniques alone or in combination with reactive milling. For example, microwave irradiation can direct energy at specific reaction surfaces to provide rapid heating and deep energy penetration of the reactants. Microwave absorbers such as metal powders, which could be used as milling media, and dipolar organic liquids may also be added to the reaction system to promote the reaction. The advantage of these techniques is that high reaction rates may occur at considerably lower processing temperature than could be obtained with resistive heating thermal techniques.

EXAMPLES

Preparation of Sodium Trihydridoaluminum-(4-Methoxy) Phenoxide (STAMP):

Under an inert atmosphere, 20 g (0.137 mol) of sodium 4-methoxyphenoxide in 100 g (113 mL) of tetrahydrofuran was added to a 300 mL high pressure reactor. Aluminum metal powder (11 g, 0.40 mol) containing 0.185% Ti was added and, the reactor sealed. The reactor was then heated to 160° C. and pressurized to 1000 psi (6.9 MPa) with hydrogen gas. After 15 min the uptake of hydrogen had ceased and the reactor was cooled and the solution filtered under an inert atmosphere to remove excess aluminum, leaving a tetrahydrofuran solution containing 1.09 M of active hydride. Active hydride is hydride that is reactive to form hydrogen.

Preparation of Stamp Using Homogeneous Titanium Catalyst:

Under an Inert Atmosphere, an anhydrous solution of 20 weight percent sodium 4-methoxyphenoxide in tetrahydrofuran was prepared. 0.1975 g of titanium tetra(n-butoxide) (0.00058 moles) was added to a 100 g portion of 20 weight percent sodium 4-methoxyphenoxide in tetrahydrofuran. 38.62 g of the titanium containing solution was then mixed with an additional 61.41 g of 20 weight percent sodium 4-methoxyphenoxide in tetrahydrofuran. The final solution was added to a 300 mL high pressure reactor. Aluminum metal powder (20 g, 0.74 mol) was added and the reactor sealed. The reactor was then pressurized to 650 psig (4.5 MPa) with hydrogen and heated to 160° C. At 160° C. the pressure was maintained at 915-925 psig (6.31-6.38 MPa) by addition of hydrogen as required. The uptake of hydrogen was initially very gradual, but increased with time. After about 450 min the uptake of hydrogen had ceased and the reactor was cooled and the solution filtered under an inert atmosphere to remove excess aluminum. The hydrogen uptake based on integration of the mass flow controller flow rate was 0.17 moles (theoretical 0.20 moles). The recovery of solids, mainly aluminum metal, was 15.78 g (0.156 moles consumed, theoretical 0.137 moles). Solution hydrolysis gave 0.44 moles of hydrogen (theoretical 0.41 moles), corresponding to 1.3 M $NaAlH_3(OR)$ solution.

Attempted Preparation of Sodium Trihydridoaluminum-(4-Methoxy)Phenoxide without Titanium:

Under an inert atmosphere, 25 g (0.171 mol) of sodium 4-methoxyphenoxide in 100 g (125 mL) of tetrahydrofuran was added to a 300 mL high pressure reactor. Aluminum metal powder (11 g, 0.40 mol) was added and the reactor sealed. The reactor was then heated to 180° C. and 1000 psi (6.9 MPa) of hydrogen gas was applied. After 4.5 h, no uptake of hydrogen was observed and the reactor was cooled and the solution filtered under an inert atmosphere to remove excess aluminum, leaving a tetrahydrofuran solution containing unreacted sodium 4-methoxyphenoxide and unreacted aluminum powder.

Effect of Ti Concentration-Addition of Soluble Ti

| Example Number | g NaMEHQ (mol) | g Al (mol) | mg Ti added | ppm Ti | ($H_2$) % conversion | total mmoles active hydride |
|---|---|---|---|---|---|---|
| 1 | 20.1 (0.137) | 20.0 (0.743) | 0 | 0 | 36.7 | 152 |
| 2 | 20.0 (0.137) | 10.0 (0.371) | 1.4 | 140 | 18.2 | 75 |
| 3 | 11.0 (0.075) | 10.0 (0.371) | 2.8 | 280 | 89.5 | 203 |
| 4 | 10.4 (0.071) | 20.0 (0.742) | 8.6 | 430 | 100.0 | 276 |
| 5 | 20.0 (0.137) | 20.0 (0.742) | 11 | 550 | 100.0 | 436 |
| 6 | 12.0 (0.082) | 10.0 (0.370) | 22 | 2200 | 100.0 | 247 |

Note:
ppm Ti is relative to the amount of Al

Examples 1-6 were prepared by loading the aluminum metal (600 μm average particle size granules, <50 ppm Ti, sodium 4-methoxyphenol and 100 g (88.9 mL) tetrahydrofuran into a 300 mL high pressure reactor along with sufficient titanium (IV) butoxide to provide the amount of titanium specified in the table. The reactor was sealed, initially pressurized to 600 psig with hydrogen, then heated to 160° C. while adjusting the hydrogen pressure so that once at temperature, a reactor pressure of 925 psig was maintained. Upon completion of the reaction, the reactor was cooled and the solution filtered under inert atmosphere to remove insolubles, leaving a tetrahydrofuran solution containing the total moles of active hydride specified.

Example 1 demonstrates that soluble hydride is produced in the absence of added titanium, however, at a low level and at low rates. In addition to the soluble product, sodium hydride (NaH) was observed at 5.4% in the unreacted aluminum, which accounts for some portion of the hydrogen conversion. Example 2 has a lower degree of hydrogen conversion relative to Example 1, however, no sodium hydride was observed in the reaction insolubles. The higher conversion found in Example 1 is most likely a result of NaH formation. The remaining examples produce much higher conversion than in Example 2 and similarly, no NaH was observed in the insoluble, unreacted aluminum.

Preparation of Sodium Borohydride:

Under an inert atmosphere, 2.3 g (5.1 mmol) of tri(4-methoxyphenoxy)-boroxine was dissolved in 15 g of 2-methyl-tetrahydrofuran (2-MeTHF). The resulting solution was then added dropwise over 15 min to 50.5 g of a magnetically stirred 2-MeTHF solution of 7.84 wt % sodium trihydridoaluminium-(4-methoxy)phenoxide (STAMP) (22.5 mmol, 1.1 equiv.) in a 100 mL Schlenk flask. During the addition, a white precipitate formed and the flask warmed. The slurry was agitated for an additional 15 minutes, then the stirring was halted and the flask was left to sit overnight to cool and allow the solids to settle. The solids were then filtered, washed with 10 mL 2-MeTHF and dried under vacuum. $^{11}B$ and $^{27}Al$ NMR confirmed that the white solids were clean sodium borohydride. Yield: 0.537 g (14.2 mmol, 93%). Purity by hydrogen evolution: 99.6%.

Recovery of 4-Methoxyphenol (MEHQ):

Under an inert atmosphere, 18.1 g of the white byproduct from the reaction to form sodium borohydride (77.3% MEHQ based on reagent input into the sodium borohydride reaction, 14.0 g, 113 mmol) was treated with 70 g of nitrogen-sparged deionized water and the resulting slurry allowed to stir for 10 min. Under positive nitrogen purge, 29.1 g of 1N aqueous hydrochloric acid solution was added stepwise to the slurry to adjust the pH to 7.00. 45 g of methyl isobutyl ketone (MIBK) was then added to the stirred slurry and the resulting mixture filtered in air. The filter cake was washed with 2×15 mL deionized water followed by 3×15 g MIBK. The collected filtrate was transferred to a separatory funnel and the upper, organic layer was collected in a 250 mL Schlenk flask. The aqueous layer was washed with 2×25 g MIBK and the combined organic fractions were vacuum evaporated to give an off-white powder. $^{1}H$ NMR confirmed that the collected solids were high purity MEHQ. Yield: 13.6 g (110 mmol, 97%).

The invention claimed is:

1. A compound of formula $M(AlH_3OR^1)_y$, wherein $R^1$ is phenyl substituted by an alkoxy group having from one to four carbon atoms; M is lithium, sodium or potassium; and y is one.

2. The compound of claim 1 in which M is sodium.

3. The compound of claim 2 in which $R^1$ is 4-methoxyphenyl.

4. A process for production of a compound of formula $M(AlH_3OR^2)_y$, wherein $R^2$ is phenyl or phenyl substituted by at least one alkyl or alkoxy group, M is an alkali metal, Be or Mg; and y is one or two; said process comprising combining a compound of formula $(R^2O)_yM$ with aluminum, hydrogen and a metallic catalyst selected from the group consisting of titanium, zirconium, hafnium, niobium, vanadium, tantalum and iron; wherein the catalyst is present at a level of at least 200 ppm based on weight of aluminum.

5. The process of claim 4 in which the metallic catalyst is titanium, zirconium, hafnium or combinations thereof.

6. The process of claim 5 in which M is lithium, sodium or potassium, and y is one.

7. The process of claim 6 in which $R^2$ is phenyl or phenyl substituted by at least one of: (i) an alkoxy group having from one to four carbon atoms; and (ii) an alkyl group having from one to four carbon atoms.

8. The process of claim 7 further comprising combining the compound of formula $MAlH_3OR^2$ with a triaryl borate or triaryl boroxine to produce an alkali metal borohydride.

\* \* \* \* \*